US010758514B2

(12) United States Patent
Liu et al.

(10) Patent No.: US 10,758,514 B2
(45) Date of Patent: Sep. 1, 2020

(54) USE OF TETRAHYDROCANNABINOL AND/OR CANNABIDIOL FOR INCREASING RADIOSENSITIVITY IN THE TREATMENT OF A BRAIN TUMOUR

(71) Applicant: GW Pharma Limited, Salisbury, Wiltshire (GB)

(72) Inventors: Wai Liu, London (GB); Katherine Scott, London (GB); Angus Dalgleish, London (GB); Marnie Duncan, Salisbury (GB); Colin Stott, Salisbury (GB)

(73) Assignee: GW Pharma Limited, Salisbury (GB)

( * ) Notice: Subject to any disclaimer, the term of this patent is extended or adjusted under 35 U.S.C. 154(b) by 0 days.

(21) Appl. No.: 15/969,422

(22) Filed: May 2, 2018

(65) Prior Publication Data

US 2019/0099398 A1 Apr. 4, 2019

Related U.S. Application Data

(63) Continuation of application No. 14/899,598, filed as application No. PCT/GB2014/051888 on Jun. 19, 2014, now abandoned.

(30) Foreign Application Priority Data

Jun. 19, 2013 (GB) .................................. 1310909.5

(51) Int. Cl.
*A61K 31/352* (2006.01)
*A61P 35/00* (2006.01)
*A61K 36/185* (2006.01)
*A61K 31/05* (2006.01)

(52) U.S. Cl.
CPC ............ *A61K 31/352* (2013.01); *A61K 31/05* (2013.01); *A61K 36/185* (2013.01); *A61P 35/00* (2018.01)

(58) Field of Classification Search
CPC .............................. A61K 31/353; A61P 35/00
See application file for complete search history.

(56) References Cited

U.S. PATENT DOCUMENTS

| | | | |
|---|---|---|---|
| 6,730,330 B2 | 5/2004 | Whittle et al. | |
| 6,946,150 B2 | 9/2005 | Whittle | |
| 7,968,594 B2 | 6/2011 | Guy et al. | |
| 8,632,825 B2 * | 1/2014 | Velasco Diez | A61K 31/05 424/725 |
| 8,790,719 B2 * | 7/2014 | Parolaro | A61K 31/05 424/725 |
| 2002/0137064 A1 | 9/2002 | Desprez et al. | |
| 2003/0021752 A1 | 1/2003 | Whittle et al. | |
| 2003/0158191 A1 | 8/2003 | Travis | |
| 2003/0166727 A1 | 9/2003 | Mechoulam et al. | |
| 2004/0039048 A1 | 2/2004 | Guzman Pastor et al. | |
| 2004/0049059 A1 | 3/2004 | Mueller | |
| 2004/0138293 A1 | 7/2004 | Werner et al. | |
| 2005/0165259 A1 | 7/2005 | Martin et al. | |
| 2006/0234273 A1 | 10/2006 | Desprez et al. | |
| 2006/0247304 A1 | 11/2006 | Guy et al. | |
| 2007/0072938 A1 | 3/2007 | Rose | |
| 2007/0203249 A1 | 8/2007 | Cerchietti | |
| 2008/0057117 A1 | 3/2008 | Werner et al. | |
| 2008/0262099 A1 | 10/2008 | Whittle et al. | |
| 2010/0204312 A1 | 8/2010 | McAllister et al. | |
| 2011/0086113 A1 | 4/2011 | Velasco Diez et al. | |
| 2011/0117216 A1 | 5/2011 | Velasco Diez et al. | |
| 2012/0225136 A1 | 9/2012 | Whittle et al. | |
| 2013/0059018 A1 | 3/2013 | Parolaro et al. | |
| 2014/0287067 A1 | 9/2014 | Velasco Diez et al. | |
| 2015/0086653 A1 | 3/2015 | Parolaro et al. | |
| 2015/0150844 A1 | 6/2015 | McAllister et al. | |
| 2015/0313867 A1 | 11/2015 | Velasco Diez et al. | |
| 2016/0136127 A1 | 5/2016 | Liu et al. | |

FOREIGN PATENT DOCUMENTS

| | | |
|---|---|---|
| CN | 1976690 A | 6/2007 |
| EP | 1177790 A1 | 2/2002 |
| EP | 1802274 B1 | 9/2008 |
| GB | 2380129 A | 4/2003 |
| GB | 2384707 A | 8/2003 |
| GB | 2386322 A | 9/2003 |
| GB | 2391865 A | 2/2004 |
| GB | 2418612 A | 4/2006 |
| GB | 2438682 A | 12/2007 |
| GB | 2439393 A | 12/2007 |
| GB | 2448535 A | 10/2008 |
| GB | 2460672 A | 12/2009 |
| GB | 2471987 A | 1/2011 |
| GB | 2478595 A | 9/2011 |
| WO | 2001/58445 A1 | 8/2001 |
| WO | 2001/87295 A1 | 11/2001 |
| WO | 2002/069993 A1 | 9/2002 |

(Continued)

OTHER PUBLICATIONS

Gilbert et al., Neuro Oncol., (2002), 4(4): p. 261-7.*
Shrieve et al., International J. of Radiation Oncology, Biology Physics, (1992), 24(4), p. 599-610.*
Scott et al., Molecular Cancer Therapeutics, (2014), 13(12), p. 2955-2967.*
Adalpe, K et al. (2006). "Models of malignant glioma," Drug Discovery Today: Disease Models 3(2):191-196.
American Association of Neurological Surgeons (AANS) (Mar. 2015). "Glioblastoma Multiforme," located at http://www.aans.org/Patient Information/Conditions and Treatments/Glioblastoma-Multiforme, last visted on Jul. 2, 2015, 4 pages.

(Continued)

*Primary Examiner* — Yong L Chu
(74) *Attorney, Agent, or Firm* — Morrison & Foerster LLP

(57) ABSTRACT

The present invention relates to the use of phytocannabinoids for increasing radiosensitivity in the treatment of cancer. Preferably the phytocannabinoids used are either tetrahydrocannabinol (THC) and/or cannabidiol (CBD). Preferably the type of cancer to be treated is glioma.

7 Claims, 4 Drawing Sheets

(56) References Cited

FOREIGN PATENT DOCUMENTS

| | | |
|---|---|---|
| WO | 2003/063847 A1 | 8/2003 |
| WO | 2004/041269 A2 | 5/2004 |
| WO | 2005/120478 A1 | 12/2005 |
| WO | 2006/037981 A1 | 4/2006 |
| WO | 2006/107903 A2 | 10/2006 |
| WO | 2008/129258 A1 | 10/2008 |
| WO | 2008/144475 A1 | 11/2008 |
| WO | 2008/146006 A1 | 12/2008 |
| WO | 2009/147438 A1 | 12/2009 |
| WO | 2009/147439 A1 | 12/2009 |
| WO | 2014/202989 A1 | 12/2014 |

OTHER PUBLICATIONS

Ben-Shabat, S. et al. (Feb. 9, 2006). "New Cannabidiol Derivatives: Synthesis, Binding to Cannabinoid Receptor, and Evaluation of Their Antiinflammatory Activity," J. Med. Chem. 49(3):1113-1117.
Blazquez, C. et al. (Jan. 2, 2003). "Inhibition of tumor angiogenesis by cannabinoids," The FASEB Journal 17: 529-531.
Blow, N. (Jul. 2007). "Cell migration: our protruding knowledge," Nat. Meth. 4(7): 589-594.
Boyden, S. (Mar. 1, 1962). "The chemotactic effect of mixtures of antibody and antigen on polymorphonuclear leucocytes," J. Exp. Med.115:453-466.
Casanova, M. L. et al. (Jan. 1, 2003). "Inhibition of skin tumor growth and angiogenesis in vivo by activation of cannabinoid receptors," J. Clinical Investigation 111 (1): 43-50.
Chang, F. et al. (Jul. 2003). "Signal transduction mediated by the Ras/Raf/MEK/ERK pathway from cytokine receptors to transcription factors: potential targeting for therapeutic intervention," Leukemia 17(7): 1263-1293.
Chou, T. et al. (1983). "Analysis of combined drug effects: a new look at a very old problem," TIPS 4:450-454.
De La Ossa, D. H. P. et al. (e-pub. Jan. 22, 2013). "Local Delivery of Cannabinoid-Loaded Microparticles Inhibits Tumor Growth in a Murine Xenograft Model of Glioblastoma Multiforme," PLOS One 8(1):e54795, pp. 1-8.
De Meijer, E. P. M. et al. (2005). "The inheritance of chemical phenotype in Cannabis sativa L. (II): Cannabigerol predominant plants," Euphytica 145:189-198.
De Petrocellis, L. et al. (May 15, 2007, e-pub. Jan. 18, 2007). "Regulation of transient receptor potential channels of melastatin type 8 (TRPM8): Effect of cAMP, cannabinoid CB1 receptors and endovanilloids," Exp. Cell Res. 313(9):1911-1920.
Declaration by Sean D. McAllister and Pierre-Yves Desprez dated Nov. 26, 2012, filed in U.S. Appl. No. 12/600,553, 19 pages.
Fernandes, M. et al. (1974). "Modification of Δ9-THC-Actions by Cannabinol and Cannabidiol in the Rat," Psychopharmacologia 38:329-338.
Friedman, H. S. et al. (Jul. 2000). "Temozolomide and Treatment of Malignant Glioma," Clin. Cancer Res. 6 (7):2585-2597.
Gallily, R. et al. (Oct. 2003). "γ-Irradiation Enhances Apoptosis Induced by Cannabidiol, a Non-psychotropic Cannabinoid, in Cultured HL-60 Myeloblastic Leukemia Cells," Leukemia & Lymphoma 44(10):1767-1773.
Galve-Roperh I. et al. (Mar. 2000). "Anti-tumoral action of cannabinoids: Involvement of sustained ceramide accumulation and extracellular signal-regulated kinase activation," Nature Medicine 6(3):313-318.
Gilbert, M. R. et al. (Oct. 2002). "A phase II study of temozolomide in patients with newly diagnosed supratentorial malignant glioma before radiation therapy," Neuro. Oncol. 4(4):261-267.
Grotenhermen, F. (2003). "Pharmacokinetics and Pharmacodynamics of Cannabinoids," Clin. Pharmacokinet. 42 (4):327-360.
Guzman, M. (Oct. 2003). "Cannabinoids: potential anticancer agents," Nat. Rev. Cancer 3(10):745-755.
Guzman, M. et al. (2001). "Control of the cell survival/death decision by cannabinoids," J. Mol. Med. 78(11):613-625.
Hayakawa, K. et al. (2003). "Cannabidiol potentiates pharmacological effects of Δ9-tetrahydrocannabinol via CB1 receptor-dependent mechanism," Brain Res. 1188:157-164.
Huang, G. et al. (Nov. 2007, e-pub. Jun. 29, 2007). "ECRG2 inhibits cancer cell migration, invasion and metastasis through the down-regulation of uPA/plasmin activity," Carcinogenesis 28(11): 2274-2281.
Hulkower, K. I. et al. (2011). "Cell Migration and Invasion Assays as Tools for Drug Discovery," Pharmaceutics. 3:107-124.
Izzo, A. A. et al. (Jan. 2008). "Increased endocannabinoid levels reduce the development of precancerous lesions in the mouse colon," J. Mol. Med. 86(1):89-98.
Jacobsson, S.O.P. et al. (Dec. 15, 2000). "Serum-Dependent Effects of Tamoxifen and Cannabinoids upon C6 Glioma Cell Viability," Biochem. Pharmacol. 60(12):1807-1813.
Jacobsson, S.O.P. et al. (Dec. 2001). "Inhibition of Rat C6 Glioma Cell Proliferation by Endogenous and Synthetic Cannabinoids. Relative Involvement of Cannabinoid and Vanilloid Receptors," J. Pharmacology and Expt. Therapeutics 299(3):951-959.
Jones, S. et al. (Dec. 2003). "Cannabinoid receptor systems: therapeutic targets for tumour intervention," Expert Opinion Ther. Targets 7(6):749-758.
Kelly, P. N. et al. (Jul. 20, 2007). "Tumor Growth Need Not Be Driven by Rare Cancer Stem Cells," Science 317 (5836):337.
Killestein, J. et al. (May 14, 2002). "Safety, tolerability, and efficacy of orally administered cannabinoids in MS," Neurology 58(9):1404-1407.
Levy, J. A. et al. (Mar. 1979). "Modulation of the metastatic frequency of a murine mammary adenocarcinoma by a synthetic cannabinoid drug," Proceedings of the American Association for Cancer Research, 15th Annual Meeting, New Orleans, LA, May 14-15, 1979, 20:155 Abstract No. 624.
Ligresti, A. et al. (Sep. 2006, e-pub. May 25, 2006). "Antitumor Activity of Plant Cannabinoids with Emphasis on the Effect of Cannabidiol on Human Breast Carcinoma," J. Pharmacol. Exp. Ther. 318(3):1375-1387.
Massi, P. et al. (Mar. 2004, e-pub. Nov. 14, 2003). "Antitumor effects of cannabidiol, a nonpsychoactive cannabinoid, on human glioma cell lines," The Journal of Pharmacology and Experimental Therapeutics 308 (3):838-845.
McAllister, S. D. (Apr. 5, 2005). "Molecular Mechanisms of Cannabinoid Antitumor Activity," Research Grant Proposal to Forbes Norris/MDA ALS Research Center, submitted as Exhibit A to Declaration by Sean D. McAllister and Pierre-Yves Desprez dated Nov. 26, 2012, filed in U.S. Appl. No. 12/600,553, 15 pages.
McAllister, S. D. (Apr. 5, 2005). Excel data reporting results of experiments for "Molecular Mechanisms of Cannabinoid Antitumor Activity," Research Grant Proposal to Forbes Norris/MDA ALS Research Center, submitted as Exhibit B to Declaration by Sean D. McAllister and Pierre-Yves Desprez dated Nov. 26, 2012, filed in U.S. Appl. No. 12/600,553, 1 page.
McAllister, S. D. et al. (Nov. 2007). "Cannabidiol as a novel inhibitor of Id-1 gene expression in aggressive breast cancer cells," Mol. Cancer Ther. 6(11):2921-2927.
Mechoulam, R. et al. (Nov. 2002). "Cannabidiol: An Overview of Some Pharmacological Aspects," J. Clin. Pharmacol. 42(11 Suppl):11S-19S.
Nakagawa, T. et al. (2007). "The combined effects of multiple chemotherapeutic agents for malignant glioma cells," J. Neurooncol. 84:31-37.
Nurmikko, T. J. et al. (Dec. 15, 2007, e-pub. Nov. 7, 2007). "Sativex successfully treats neuropathic pain characterised by allodynia: A randomised, double-blind, placebo-controlled clinical trial," Pain 133(1-3):210-220.
Patentee's Response and Amended Claim Set, filed in relation to the Examination report for EP09757810.8, dated Sep. 27, 2013, 5 pages.
Pertwee, RG (Jan. 2008, e-pub Sep. 10, 2007). "The diverse CB1 and CB2 receptor pharmacology of three plant cannabinoids: Δ9-tetrahydrocannabinol, cannabidiol and Δ9-tetrahydrocannabivarin," Br. J. Pharmacol. 153 (2):199-215.
Portella, G. et al. (Sep. 2003). "Inhibitory effects of cannabinoid CB1 receptor stimulation on tumor growth and metastatic spread-

(56) References Cited

OTHER PUBLICATIONS ing: actions on signals involved in angiogenesis and metastasis," The FASEB Journal: Official Publication of the Federation of American Societies for Experimental Biology 17(12):1771-1773.
Pouliot, N. et al. (2012). "Investigating Metastasis Using In Vitro Platforms," Chapter in Metastatic Cancer: Integrated Organ System and Biological Approach, Jandial, R. et al. ed., Landes Bioscience, pp. 1-24.
Programme 10th Reunion Anual Sociedad Espanola de Investigacion sobre Cannabinoides (10th Annual Meeting of the Spanish Society for the Investigation of Cannabinoids) (Nov. 26-28, 2009). Santander, located at http://www.seic.es/reunion-anual-seic last visited on Oct. 25, 2016, 9 pages.
Robins, H. I. et al. (Jan. 2006). "Phase 2 trial of radiation plus high-dose tamoxifen for glioblastoma multiforme: RTOG protocol BR-0021," Neuro. Oncol. 8(1):47-52.
Russo, E. et al. (Feb. 2006, e-pub. Oct. 4, 2005). "A tale of two cannabinoids: The therapeutic rationale for combining tetrahydrocannabinol and cannabidiol," Med. Hypotheses. 66(2):234-246.
Sarfaraz, S. et al. (Mar. 1, 2005). "Cannabinoid Receptor as a Novel Target for the Treatment of Prostate Cancer," Cancer Res. 65(5):1635-1641.
Shrieve, D. C. et al. (1992). "Hyperfractionated radiation therapy for gliomas of the brainstem in children and in adults," Int. J. Radiation Oncol. Biol. Phys. 24(4):599-610.
Soroceanu, L. et al. (Oct. 2009). "The role of ID-1 in modulating brain tumor invasion and dispersal," Neuro-Oncology 11:564 Abstract No. 3, submitted as Exhibit C to Declaration by Sean D. McAllister and Pierre-Yves Desprez dated Nov. 26, 2012, filed in U.S. Appl. No. 12/600,553, 1 page.
Statement of Opposition filed by Elkington and Fife LLP, in relation to EP 11709175.1, dated Nov. 7, 2016, 12 pages.
Strasser, F. et al. (Jul. 20, 2006). "Comparison of Orally Administered Cannabis Extract and Delta-9-Tetrahydrocannabinol in Treating Patients with Cancer-Related Anorexia-Cachexia Syndrome: A Multicenter, Phase III, Randomized, Double-Blind, Placebo-Controlled Clinical Trial From the Cannabis-In-Cachexia-Study-Group," J. Clin. Oncol. 24(21):3394-3400.
The United Kingdom Parliament, Select Committee on Science and Technology (1998). "Ninth Report," located at http://www.parliament.the-stationery-office.co.uk/pa/Id199798/Idselect/Idsctech/151/15101.htm, last visited on Dec. 21, 2006, 43 pages.
The United Kingdom Parliament, Select Committee on Science and Technology (Mar. 14, 2001). "Second Report," located at http://www.publications.parliament.uk/pa/Id200001/Idselect/Idsctech/50/5001.htm, last visited on Jan. 10, 2007, 10 pages.
Torres, S. et al. (Jan. 2011). "A Combined Preclinical Therapy of Cannabinoids and Temozolomide Against Glioma," Mol. Cancer Ther. 10(1):90-103.
Tucker, A. N. et al. (Aug. 1977). "Effects of cannabinoids on L1210 murine leukemia, 1. Inhibition of DNA synthesis," Res. Commun. in Chem. Pathol. Pharmacol. 17(4):703-714.

Vaccani, A. et al. (Apr. 2005). "Cannabidiol inhibits human glioma cell migration through a cannabinoid receptor-independent mechanism," British Journal of Pharmacology 144(8):1032-1036.
Velasco, G. et al. (Aug. 2007, e-pub Jun. 28, 2007). "Cannabinoids and gliomas," Mol. Neurobiol. 36(1):60-67.
Velasco, G. et al. (Sep. 2004). "Hypothesis: cannabinoid therapy for the treatment of gliomas?," Neuropharmacology 47:315-323.
Verbraecken, J. et al. (Apr. 2006). "Body surface area in normal-weight, overweight, and obese adults: A comparison study," Metabolism Clinical and Experimental 55(4):515-524.
Zhongshi, S. et al. (2004) "The New Development of Anti-tumor Drug," Evaluation and Analysis of Drug Use in Hospitals of China 4(1), 8 pages.
Guzman et al., (2006). "A pilot clinical study of delta.9-tetrahydrocannabinol in patients with recurrent glioblastoma multiforme," British Journal of Cancer, 95(2):197-203.
Kenyon et al., (2018). "Report of Objective Clinical Responses of Cancer Patients to Pharmaceutical-grade Synthetic Cannabidiol," AntiCancer Research, 38:5831-5835.
Kogan, (2005). "Cannabinoids and Cancer," Mini-Reviews in Medicinal Chemistry, 5:941-952.
Liu et al., (2010). "Cannabis-Derived Substances in Cancer Therapy—An Emerging Anti-Inflammatory Role for the Cannabinoids," Current Clin. Pharmacology 5:281-287.
Marcu et al., (2010). "Cannabidiol Enhances the Inhibitory Effects of $\Delta$9-Tetrahydrocannabinol on Human Glioblastoma Cell Proliferation and Survival," Mol Cancer Ther 9(1):180-189.
Massi et al., (2006). "The non-psychoactive cannabidiol triggers caspase activation and oxidative stress in human glioma cells," Cell. Mol. Life Sci. 63:2057-2066.
Massi et al., (2008). "5-Lipoxygenase and anandamide hydrolase (FAAH) mediate the antitumor activity of cannabidiol, a non-psychoactive cannabinoid," J. Neurochemistry 104:1091-1100.
McPartland et al., (2001). "Cannabis and Cannabis Extracts: Greater Than the Sum of Their Parts?" J. Cannabis Therapeutics in HIV/AIDS 103-132.
Sánchez et al., (1998). "$\Delta$9-Tetrahydrocannabinol induces apoptosis in C6 glioma cells," FEBS Letters 436:6-10.
Sánchez et al., (2001). "Inhibition of Glioma Growth in Vivo by Selective Activation of the CB2 Cannabinoid Receptor," Cancer Research 61:5784-5789.
Scott et al., (2013). "Enhancing the Activity of Cannabidiol and Other Cannabinoids In Vitro Through Modifications to Drug Combinations and Treatment Schedules," Anticancer Research, 33:4373-4380.
Scott et al., (2014). "The Combination of Cannabidiol and $\Delta$9-Tetrahydrocannabinol Enhances the Anticancer Effects of Radiation in an Orthotopic Murine Glioma Model," Mol Cancer Ther., 13(12):2955-67.
Scott et al., (2015). "Inhibiting Heat Shock Proteins Can Potentiate the Cytotoxic Effect of Cannabidiol in Human Glioma Cells," Anticancer Research, 35:5827-5838.
Thomas et al., (2007). "Cannabidiol displays unexpectedly high potency as an antagonist of CB1 and CB2 receptor agonists in vitro," British J. of Pharmacology 150:613-623.

\* cited by examiner

USE OF TETRAHYDROCANNABINOL AND/OR CANNABIDIOL FOR INCREASING RADIOSENSITIVITY IN THE TREATMENT OF A BRAIN TUMOUR

The present invention relates to the use of phytocannabinoids for increasing radiosensitivity in the treatment of cancer. Preferably the phytocannabinoids used are either tetrahydrocannabinol (THC) and/or cannabidiol (CBD).

BACKGROUND TO THE INVENTION

Cancer is a disease in which a group of cells display the traits of uncontrolled growth. This means that the cells grow and divide beyond the levels of normal limits. The cells are also able to invade and destroy surrounding tissues. In addition cancer cells sometimes also metastasize, meaning that they spread to other locations in the body via the blood or lymph.

Most cancers are caused by abnormalities in the genetic material of the cells. These abnormalities may be due to the effects of carcinogens. Other cancer-promoting genetic abnormalities may be randomly acquired through errors in DNA replication, or are inherited, and thus present in all cells from birth.

Genetic abnormalities found in cancer typically affect two general classes of genes. Cancer-promoting oncogenes are often activated in cancer cells, giving those cells new properties, such as hyperactive growth and division, protection against programmed cell death, loss of respect for normal tissue boundaries, and the ability to become established in diverse tissue environments.

Tumour suppressor genes are often inactivated in cancer cells, resulting in the loss of normal functions in those cells, such as accurate DNA replication, control over the cell cycle, orientation and adhesion within tissues, and interaction with protective cells of the immune system.

There are many different types of cancer and the cancer s usually classified according to the type of tissue from which it originated.

Cancer is usually treated by one or more of the following: surgery, chemotherapy, radiation therapy, immunotherapy and monoclonal antibody therapy. The type of therapy depends upon the location and grade of the tumour and the stage of the disease.

Complete removal of the cancer without damage to the rest of the body is the goal of treatment. Sometimes this can be accomplished by surgery, but the propensity of cancers to invade adjacent tissue or to spread to distant sites by microscopic metastasis often limits its effectiveness. The effectiveness of chemotherapy is often limited by toxicity to other tissues in the body. Radiation can also cause damage to normal tissue.

Cancers are known to affect many areas of the body with the most common types of cancers including: cancer of the bile duct, cancer of the bladder, cancer of the bone, cancer of the bowel (including cancer of the colon and cancer of the rectum), cancer of the brain, cancer of the breast, cancer of the neuroendocrine system (commonly known as a carcinoid), cancer of the cervix, cancer of the eye, cancer of the oesophagus, cancer of the head and neck (this group includes carcinomas that start in the cells that form the lining of the mouth, nose, throat, ear or the surface layer covering the tongue), Kaposi's sarcoma, cancer of the kidney, cancer of the larynx, leukaemia, cancer of the liver, cancer of the lung, cancer of the lymph nodes, Hodgkin's lymphoma, non-Hodgkin's lymphoma, melanoma, mesothelioma, myeloma, cancer of the ovary, cancer of the pancreas, cancer of the penis, cancer of the prostate, skin cancer, soft tissue sarcomas, cancer of the spinal cord, cancer of the stomach, testicular cancer, cancer of the thyroid, cancer of the vagina, cancer of the vulva and cancer of the uterus.

A tumour that develops in the brain can destroy or damage brain cells by producing inflammation, compressing other parts of the brain, inducing cerebral oedema (brain swelling) and can cause increases in intracranial pressure (pressure within the skull).

Each year, approximately 4300 people in the UK are diagnosed with a brain tumour. A primary brain tumour is a mass created by the growth or uncontrolled proliferation of cells in the brain. Malignant primary brain tumours are most likely to cause problems by spreading into the normal brain tissue which surrounds them and causing pressure and damage to the surrounding areas of the brain. These tumours rarely spread outside the brain to other parts of the body. However, secondary brain tumours occur when cancer cells from other parts of the body, such as the lung or breast spread to the brain.

Surgery is the treatment option of choice for many brain tumours. Some may be completely excised, but those that are deep or that infiltrate brain tissue may be debulked rather than removed.

Radiation therapy and/or chemotherapy may be recommended depending on the type of tumour involved.

Glioma cell tumours can often be lethal. The characteristic diffuse infiltrative tumour growth of gliomas often makes the surgical removal of them impossible and this profoundly complicates the clinical management of these patients.

Glioblastoma multiforme (GBM) is the most common and most aggressive type of primary brain tumour and accounts for 52% of all primary brain tumour cases and 20% of all intracranial tumours.

Different approaches are being researched in order to improve the mortality rate of patients diagnosed with a glioma. These include therapies that target the glioma cells but leave normal cells unharmed, methods that limit the spread of the cancer cells and treatments that block the tumours life-sustaining molecules.

One such area of research involves the use of phytocannabinoids as anti-tumoural agents.

Phytocannabinoids are the active constituents of *cannabis* plants and they have been found to demonstrate numerous pharmacological properties.

For example EP1177790 (Guzman et al.) describes the treatment of cerebral tumours by the administration of a natural or synthetic cannabinoid, specifically THC. It is claimed that activation of specific receptors leads to selective death of the transformed cells.

Recently the phytocannabinoid CBD has been shown to possess anti-tumoural properties (Massi et al, 2004). The work described by this paper describes anti-proliferative effects both in-vitro using U87 and U373 human glioma cell lines and in-vivo using U87 human glioma cells subcutaneously implanted to nude mice.

Malignant gliomas are highly infiltrative and proliferative tumours, which follow a characteristic pattern of growth. Glioma cells invade the adjacent normal brain structures and surrounding large blood vessels.

In addition the applicant's earlier patent EP1802274 describes the use of the cannabinoid CBD to impede the progress of cancer cells migrating from their primary tumour location to a secondary site.

Furthermore the patent applications WO 2009/147439 and WO 2009/147438 respectively describe the use of a combination of the phytocannabinoids THC and CBD and the combination of the phytocannabinoids THC and CBD with chemotherapeutic agents in the treatment of glioma.

BRIEF SUMMARY OF THE DISCLOSURE

In accordance with a first aspect of the present invention there is provided the use of the phytocannabinoids (tetrahydrocannabinol) THC and/or (cannabidiol) CBD to increase radiosensitivity in the treatment of a brain tumour.

Preferably the brain tumour is a glioma tumour. More preferably the brain tumour is a glioblastoma multiforme (GBM).

Preferably the phytocannabinoids are in the form of an extract or botanical drug substance. Alternatively the phytocannabinoids are in an isolated or pure form.

The ratio of THC to CBD used may be in the range of from 99:1 to 1:99 (THC:CBD). Preferably the ratio of THC:CBD is from 20:1 to 1:20 (THC:CBD). More preferably the ratio of THC:CBD is from 5:1 to 1:5 (THC:CBD). More preferably still the ratio of THC:CBD is substantially 1:1.

In accordance with a second aspect of the present invention there is provided the use of a combination of the phytocannabinoids tetrahydrocannabinol) THC and (cannabidiol) CBD to increase radiosensitivity in the treatment of a brain tumour.

In this specification the following terms are used and are intended to have the following meanings/definitions:

"Cannabinoids" are a group of compounds including the endocannabinoids, the phytocannabinoids and those which are neither endocannabinoids nor phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the *cannabis* plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the *cannabis* plant. Examples include WIN 55212 and SR141716 (rimonabant).

An "isolated phytocannabinoid" is one which has been extracted from the *cannabis* plant and purified to such an extent that substantially all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Guidance, June 2004, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of *cannabis*, BDS derived from *cannabis* plants do not include highly purified Pharmacopoeial grade cannabinoids The structure of the phytocannabinoids, CBD and THC are as shown below

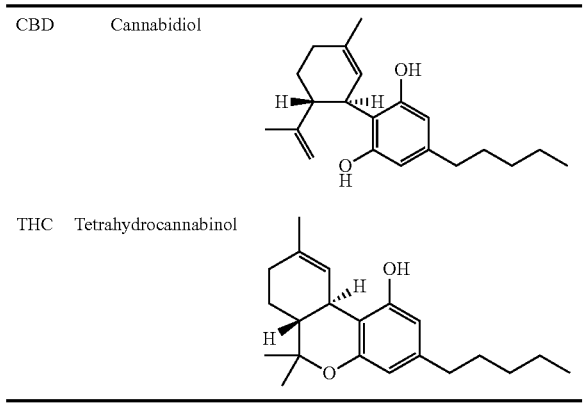

The term "increase radiosensitivity" refers to the ability of the phytocannabinoids to enhance the activity of irradiation provided during treatment for cancer.

BRIEF DESCRIPTION OF THE DRAWINGS

Embodiments of the invention are further described hereinafter with reference to the accompanying drawings, in which.

DETAILED DESCRIPTION

Figure 1:
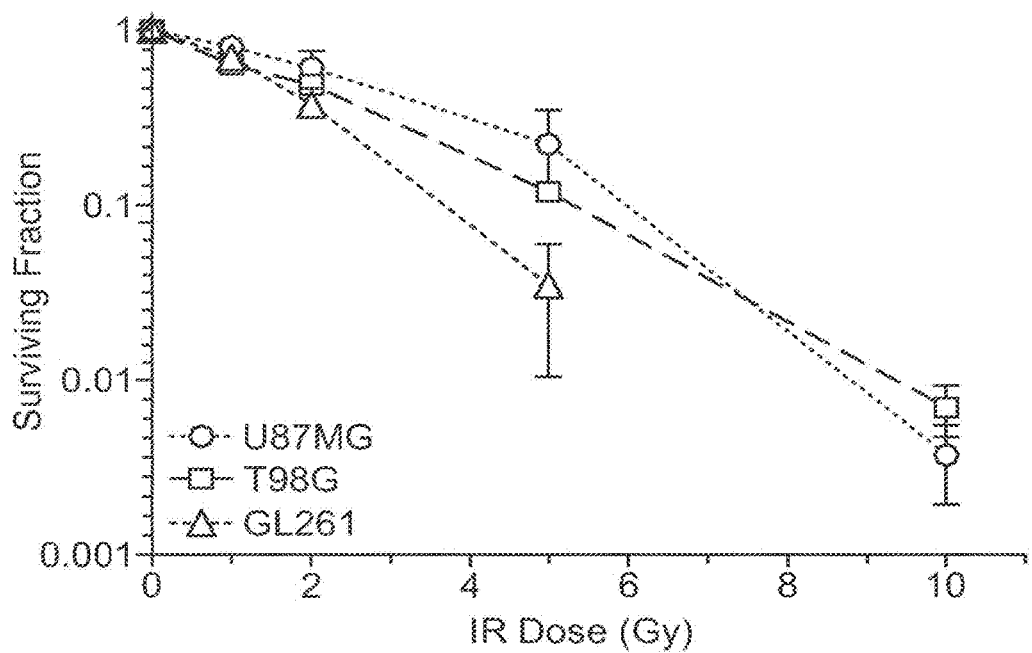
FIG. 1 shows the radiosensitivity of glioma cell lines.

The Example below describes the effect of using phytocannabinoids to increase radiosensitivity in glioma cells.

Example 1: Combination of Phytocannabinoids with Radiation

Materials and Methods
Radiosensitivity of Glioma Cell Lines

An initial dose response experiment was carried out to determine the radiosensitivity of the individual cell lines.

The human glioma cell lines T98G and U87MG were obtained from ATCC, and were lines derived from patients with a glioblastoma multiforme tumour and a glioblastoma astrocytoma respectively.

The mouse glioma cell line GL261, which is syngeneic to the C57BL/6 mouse was acquired from the NCI.

Cells were exposed to increasing doses of irradiation and then clonogenic cell survival assays were performed. The ability of the cells to survive an irradiation insult and go on and divide indefinitely forming a colony was assessed in this manner and used as our read-out of radiosensitivity.

Cells were initially seeded into flasks and left to adhere overnight. The following day they were irradiated with increasing doses of radiation (0, 1, 2, 5, 10 and 20 Gy) using $Cs^{137}$ as a radiation source. Cells were then harvested, counted and seeded again at increasing densities in 6-well plates, adjusting the density appropriately for the radiation dose, and then incubated for approximately 14 days. At this time, plates were washed and fixed in 70% ethanol, and colonies were stained with 5% methylene blue. Colonies consisting of >50 cells were counted and calculated as a proportion of the number of cells initially seeded (surviving fraction). This value is then used to calculate the radiosensitivity of the cell line. Data represents mean±SD of three independent experiments.

Effect of CBD on the Radiosensitivity of Glioma Cell Lines

Cells were treated with pure CBD for 24 h prior to irradiation to determine whether the single phytocannabinoids were able to prime cells to irradiation.

Cells were initially seeded into flasks and left to adhere overnight. The following day they were treated with increasing concentrations of pure CBD and then left for 24 hours. Cells were then irradiated with increasing doses of radiation (0, 1, 2 and 5 Gy) using $Cs^{137}$ as a radiation source. Cells were then harvested, counted and seeded again at increasing densities in 6-well plates, adjusting the density appropriately for the radiation dose, and then incubated for approximately 14 days. At this time, plates were washed and fixed in 70% ethanol, and colonies were stained with 5% methylene blue. Colonies consisting of >50 cells were counted and surviving fraction was calculated. Data represents mean of three independent experiments except for GL261 which is only one data set.

Effect of THC on the Radiosensitivity of Glioma Cell Lines

Cells were treated with pure THC for 24 h prior to irradiation to determine whether the single phytocannabinoids were able to prime cells to irradiation.

Cells were initially seeded into flasks and left to adhere overnight. The following day they were treated with increasing concentrations of pure THC and then left for 24 hours. Cells were then irradiated with increasing doses of radiation (0, 1, 2 and 5 Gy) using $Cs^{137}$ as a radiation source. Cells were then harvested, counted and seeded again at increasing densities in 6-well plates, adjusting the density appropriately for the radiation dose, and then incubated for approximately 14 days. At this time, plates were washed and fixed in 70% ethanol, and colonies were stained with 5% methylene blue. Colonies consisting of >50 cells were counted and surviving fraction was calculated. Data represents mean of three independent experiments.

Effect of Combining THC and CBD on the Radiosensitivity of Glioma Cell Lines

The impact of using a combination of pure THC and pure CBD on the radiosensitivity of the cell lines was then assessed. The effect of drugs prior to exposure to irradiation was assessed; therefore the phytocannabinoids THC and CBD were combined at a ratio of 1:1, and applied to cells 24 h prior to irradiation.

Cells were initially seeded into flasks and left to adhere overnight. The following day they were treated with increasing either pure THC, pure CBD or an equimolar 1:1 combination of both and then left for 24 hours. Cells were then irradiated with increasing doses of radiation (0, 1, 2 and 5 Gy) using $Cs^{137}$ as a radiation source. Cells were then harvested, counted and seeded again at increasing densities in 6-well plates, adjusting the density appropriately for the radiation dose, and then incubated for approximately 14 days. At this time, plates were washed and fixed in 70% ethanol, and colonies were stained with 5% methylene blue. Colonies consisting of >50 cells were counted and surviving fraction was calculated. Data from one data set only.

All phytocannabinoids reported here were used at molar concentrations, determined by masses of the substances received.

Results

FIG. 1 shows that the GL261 cell line is the most radiosensitive and that the human glioma cell lines were equally as sensitive.

Figure 2:
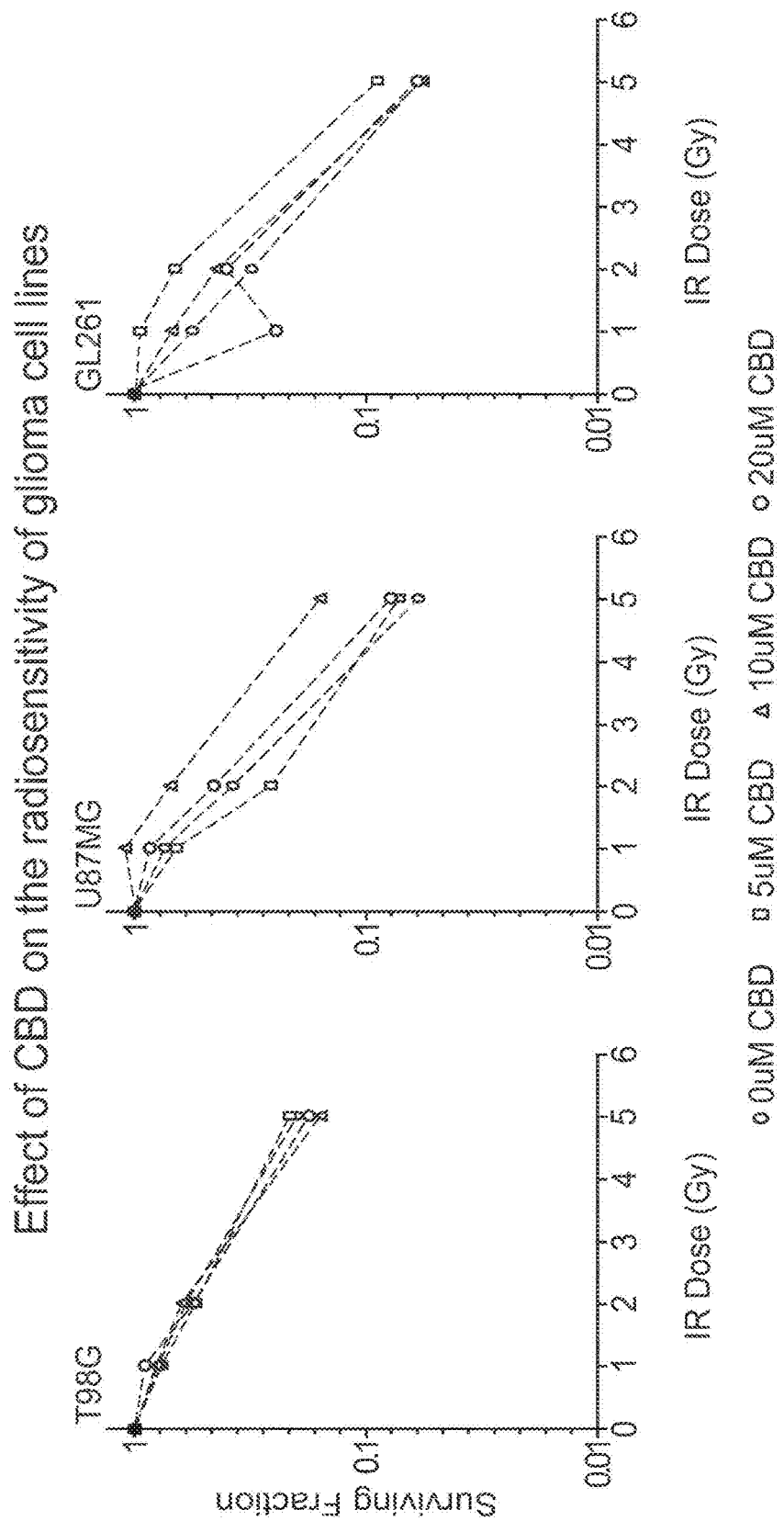
FIG. 2 which shows the effect of CBD on the radiosensitivity of glioma cell lines.
Figure 3:
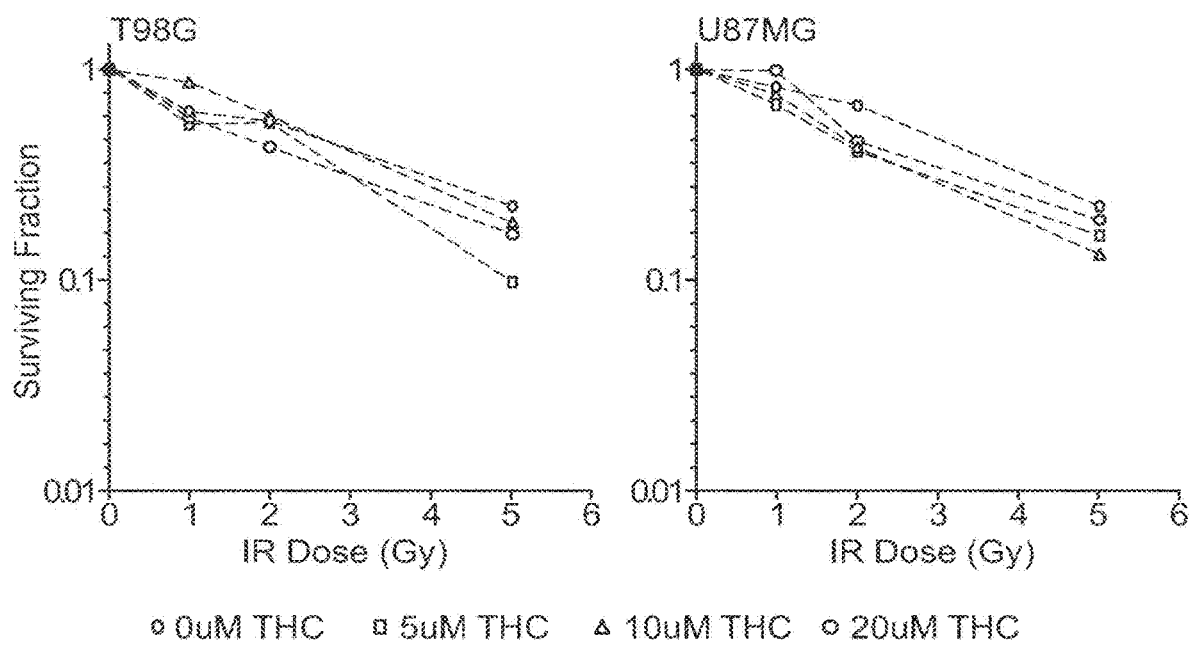
FIG. 3 which shows the effect of THC on the radiosensitivity of glioma cell lines.

FIG. 2 shows the impact of CBD on radiosensitivity, while FIG. 3 shows data for the impact of THC on radiosensitivity. Results suggested that the phytocannabinoids, when used alone, did not appear to alter the radiosensitivity of the cell lines, as there is no dose dependent effect on the surviving fraction.

Figure 4:
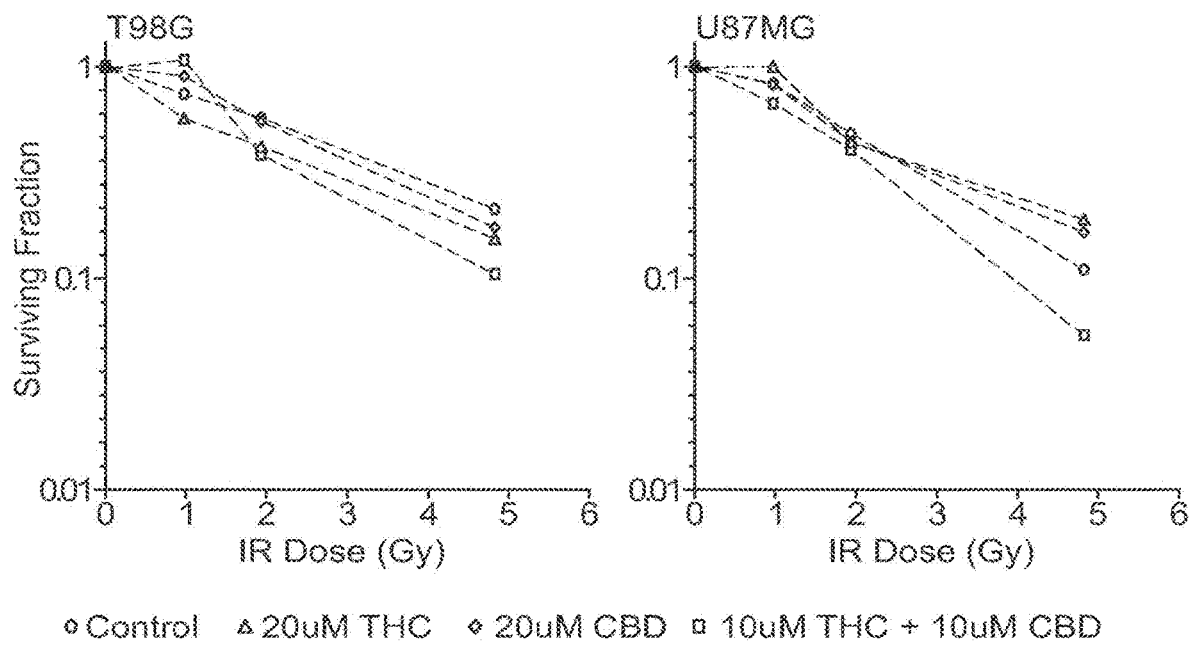
FIG. 4 which show the effect of combining THC and CBD on the radiosensitivity of glioma cell lines.

FIG. 4 shows that a combination of THC and CBD at a final concentration of 20 µM may enhance the activity of irradiation, compared to using the agents alone.

CONCLUSION

The combination of phytocannabinoids THC and CBD enhances the effect of the radiation and as such is a valuable treatment option in this difficult to treat disease.

The invention claimed is:

1. A method for increasing radiosensitivity of glioma tumour cells, comprising:
   administering a combination of tetrahydrocannabinol (THC) and cannabidiol (CBD); and
   administering radiation therapy,
wherein the combination of THC and CBD is administered prior to administering the radiation therapy, and the combination of THC and CBD administered increases radiosensitivity of the glioma tumour cells.

2. The method of claim 1, wherein the combination of THC and CBD, and the radiation therapy are administered to a human having a glioma tumour.

3. The method of claim 1, wherein the combination of THC and CBD, and the radiation therapy are administered to a human having glioblastoma multiforme (GBM).

4. The method of claim 1, wherein one of the THC or CBD, or both in the combination are present in an extract obtained from a *cannabis* plant.

5. The method of claim 1, wherein one of the THC or CBD, or both in the combination are in the form of a botanical drug substance.

6. The method of claim 1, wherein one of the THC or CBD, or both in the combination are in an isolated or pure form.

7. The method of claim 1, wherein the combination of THC and CBD is administered in a ratio of 1:1.

* * * * *